(12) United States Patent
Moberg et al.

(10) Patent No.: US 9,897,550 B2
(45) Date of Patent: Feb. 20, 2018

(54) PROBE FOR GAS SENSOR WITH GAS SPLIT SAMPLE GAS FLOW

(71) Applicant: DANFOSS IXA A/S, Vejle (DK)

(72) Inventors: Carsten Moberg, Brenderup (DK); Allan Skouboe, Horsens (DK); Jesper Høyer, Vejle (DK)

(73) Assignee: Danfoss IXA A/S, Vejle (DK)

( * ) Notice: Subject to any disclaimer, the term of this patent is extended or adjusted under 35 U.S.C. 154(b) by 0 days.

(21) Appl. No.: 15/318,719

(22) PCT Filed: Jun. 17, 2015

(86) PCT No.: PCT/EP2015/063594
§ 371 (c)(1),
(2) Date: Dec. 14, 2016

(87) PCT Pub. No.: WO2015/193374
PCT Pub. Date: Dec. 23, 2015

(65) Prior Publication Data
US 2017/0122877 A1 May 4, 2017

(30) Foreign Application Priority Data

Jun. 19, 2014 (DK) .................................. 201400323

(51) Int. Cl.
*G01N 1/00* (2006.01)
*G01N 21/85* (2006.01)
(Continued)

(52) U.S. Cl.
CPC ......... *G01N 21/8507* (2013.01); *G01N 21/15* (2013.01); *G01N 21/27* (2013.01); *G01N 2021/151* (2013.01)

(58) Field of Classification Search
CPC .......... G01N 21/8507; G01N 21/3504; G01N 21/274; G01N 2201/062;
(Continued)

(56) References Cited

U.S. PATENT DOCUMENTS

2008/0283753 A1   11/2008   Jensen et al.
2012/0033219 A1*   2/2012   Hokamura ............. G01N 21/15
                                                            356/438
(Continued)

FOREIGN PATENT DOCUMENTS

EP    1 944 598 A1    7/2008
EP    2 604 999 A1    6/2013
(Continued)

OTHER PUBLICATIONS

International Search Report for PCT U.S. Appl. No. PCT/EP2015/063594 dated Oct. 5, 2015.

*Primary Examiner* — Michael P Stafira
(74) *Attorney, Agent, or Firm* — McCormick, Paulding & Huber LLP

(57) ABSTRACT

A probe for an IR or UV sensor comprising a light emitter and detector is described comprising a lens. The detector detects the spectrums of the emitted light after it has passed a gas to be measured. The sensor of the present invention is especially suitable for such as harsh or aggressive environments measuring the exhaust gasses, for example in ships, vehicles, chimneys etc., and comprises purge gas protections for delicate optical parts to prevent particles etc. from the exhaust gas depositing on the optics. The sensor further has a flow of sample gas from the gas to be measured being adapted to prevent the purge gas from inferring with the measurements where the sample gas are split into at least two flows where one is adapted for preventing the purge gas from influencing the measurement in a measuring region.

20 Claims, 4 Drawing Sheets

(51) Int. Cl.
*G01N 21/15* (2006.01)
*G01N 21/27* (2006.01)

(58) Field of Classification Search
CPC ... G01N 2021/3148; G01N 2021/3181; G01N 2021/8514; G01N 21/15; G01N 21/31; G01N 21/314; G01N 21/3151; G01N 21/35; G01N 21/3577
See application file for complete search history.

(56) References Cited

U.S. PATENT DOCUMENTS

2014/0183380 A1* 7/2014 Ukon ................ G01N 21/3504
250/573
2016/0047718 A1* 2/2016 Uratani ............... G01M 15/102
73/114.71

FOREIGN PATENT DOCUMENTS

EP     2 610 607 A1    7/2013
GB     2 274 332 A     7/1994

* cited by examiner

PROBE FOR GAS SENSOR WITH GAS SPLIT SAMPLE GAS FLOW

CROSS REFERENCE TO RELATED APPLICATION

This application is entitled to the benefit of and incorporates by reference subject matter disclosed in the International Patent Application No. PCT/EP2015/063594 filed on Jun. 17, 2015 and Danish Patent Application No. PA201400323 filed on Jun. 19, 2014.

TECHNICAL FIELD

A probe for an IR or UV sensor comprising a light emitter and detector is described comprising a lens. The detector detects the spectrums of the emitted light after it has passed a gas to be measured. The sensor of the present invention is especially suitable for such as harsh or aggressive environments measuring the exhaust gasses, for example in ships, vehicles, chimneys etc., and comprises purge gas protections for delicate optical parts to prevent particles etc. from the exhaust gas depositing on the optics. The sensor further has a flow of sample gas from the gas to be measured being adapted to prevent the purge gas from inferring with the measurements where the sample gas are split into at least two flows where one is adapted for preventing the purge gas from influencing the measurement in a measuring region.

BACKGROUND

One example of gas sensor based on measuring the spectrum absorptions of emitted light by a gas is described in US 2008/0283753, wherein the pass band of a first filter is arranged within the pass band of a second filter and the evaluating device forms the difference of the signals and normalizes it to the signal.

Using such a sensor in relatively harsh environments such as exhaust systems in ships, vehicles etc. will however expose the delicate parts environment within the exhaust stack that may comprise a wide range of particles and gasses that could damage them, or just reduce their lifetime. One option would be to protect the parts with sight glasses such that they becomes isolated from the harsh environment, but the transparency of these may then be reduced over time by settlement of particles etc.

Another example of a gas sensor is to be found in EP 2 604 999 disclosing a gas analyser for the absorption-spectroscopic in-situ determination of at least one chemical and/or physical parameter of a gaseous measurement medium, wherein the gas analyser includes a first housing; at least one laser as a radiation source, which laser is arranged in the first housing; at least one first process window for coupling the radiation emitted by the laser into a measurement medium; and at least one detector by which, following interaction with the measurement medium, the radiation is detected. The sensor includes openings in the side of the probe the gas thus passing directly from the outside of the probe transversing the measuring area of the probe directly through these openings under the outside flow conditions such as flow rates of the gasses to that of the inside of the probe. This has some disadvantages in that there is no control of the flows and conditions within the measuring region of the probe such as the exchange rate of gasses.

SUMMARY

The present invention introduces a probe overcoming such problems.

The present invention relate to a probe for gas sensor where said sensor is adapted to measure the concentration of at least one substance of a sample gas based on spectrum absorption, said probe comprising a light path passing a measuring region in at least two flows, where the one flow may pass the measuring region in the area close to the outlet section of a purge gas volume thus ensuring to remove it before entering into the main part of the measuring region disturbing the measurements.

To ensure there is no direct of the measuring region to the gas containing environment, such that harsh environment such that the flow conditions etc. is controllable and, enabling a regulation of the respective flows of gas to the measuring region, either to make them uniform, or to make some or all of them different, the probe comprises a sample inlet being in flow communication with the flow of gas to be measured, and where this sample inlet is in flow communication with a sample gas conduit which splits into a first branch and a second branch splitting the sample gas into the at least two flows, and where sample inlet is positioned such that the flow of gas to be measured does not tend unguided to flow into the sample inlet. The sample inlet thus is not positioned in the direction of the flow of gas to be measured, but rather the sample gas enters the probe from the sample inlet in a transverse direction with an angle compared to the flow direction of the gas to be measured being higher than or equal to about 45 degrees.

A third branch may be introduced such that a third flow is formed, the two flow then may be positioned close to purge gas outlets to remove the incoming purge gasses whereas a third may be situated between them to ensure to fill out the measuring region with sample gas.

To ensure a quick removing of the entering purge gasses where the sample gas transverse the measuring region in the areas close to the purge gas outlets transverses the measuring region with an angle in the range of 45 degrees. The third flow may pass with an angle to the light path being higher than or equal to 45 degrees, it is thus ensured the gas to be measured fills the whole width of the measuring region without having to ensure distribution.

To regulate the relative flow rates the first, second and an optional third branch being the inlets to the measuring region for the first, second and the optional have relative different flow restrictions.

To prevent particles in the measuring region from getting into contact with delicate (optical) parts the light path further passes a purge gas volume(s) where purge gas flow in the purge gas volume(s) forming a gas barrier preventing particles in the measuring region) from passing the end of the purge gas volume(s) distal to the measuring region where the delicate parts are situated, such as lens and reflector. The system may comprise a first such purge gas volume, a second such purge gas volume and more, this being dependent on the number and positions of the delicate parts.

In one embodiment of the present invention the sample gas enters the measuring region in at least two flows, where the first flow are feed into the measuring region in the area close to the first purge gas volume and the second flow are feed into the measuring region in the area close to the second purge gas volume, thereby is obtained that the purge gas entering the measuring region are removed and thus does not change the concentration of gas to be measured present in the measuring region that could make unreliable measurements.

To ensure full distribution of the sample gas in the measuring region the probe in one further embodiment comprises a third flow of the sample gas being feed into the measuring region between the first and second flows. To even further ensure distribution the main first flow leaves the measuring region through a first outlet and the main second and third flows leaves the measuring region through a common second outlet.

DETAILED DESCRIPTION

Figure 1:
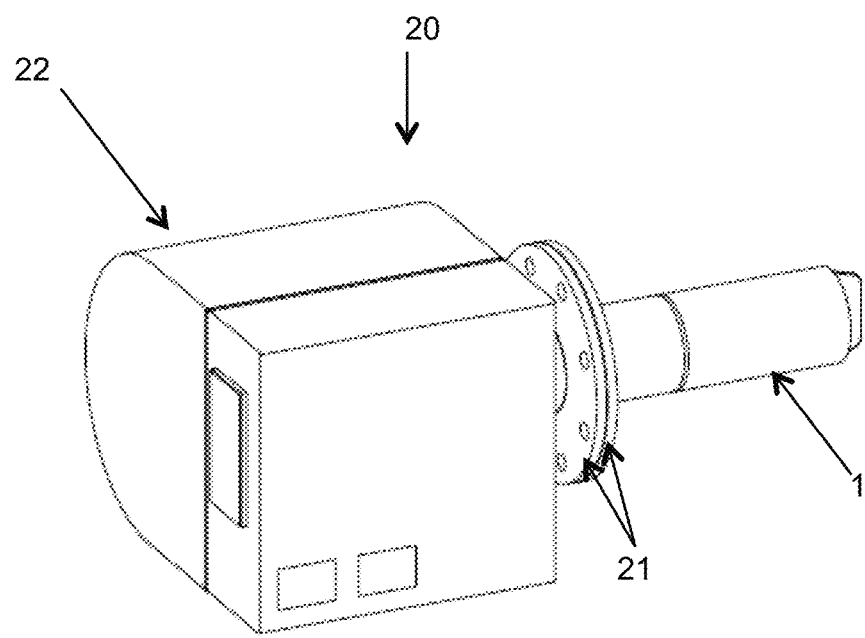
FIG. 1 Sensor according to the present invention comprising a back-end and a probe.

FIG. 1 shows an external view of a sensor (20) with a back-end (22) and a probe (1) according to the present invention where the probe part (1) is adapted to be inserted in connection with e.g. an exhaust gas. The probe (1) is attached to the sensor (20) by flanges (21) of the probe (1) and sensor (20) respectively having openings where nuts and bolts may be used to fix the two parts together. Any other means to attach the parts would however also apply to the present invention.

Figure 2:
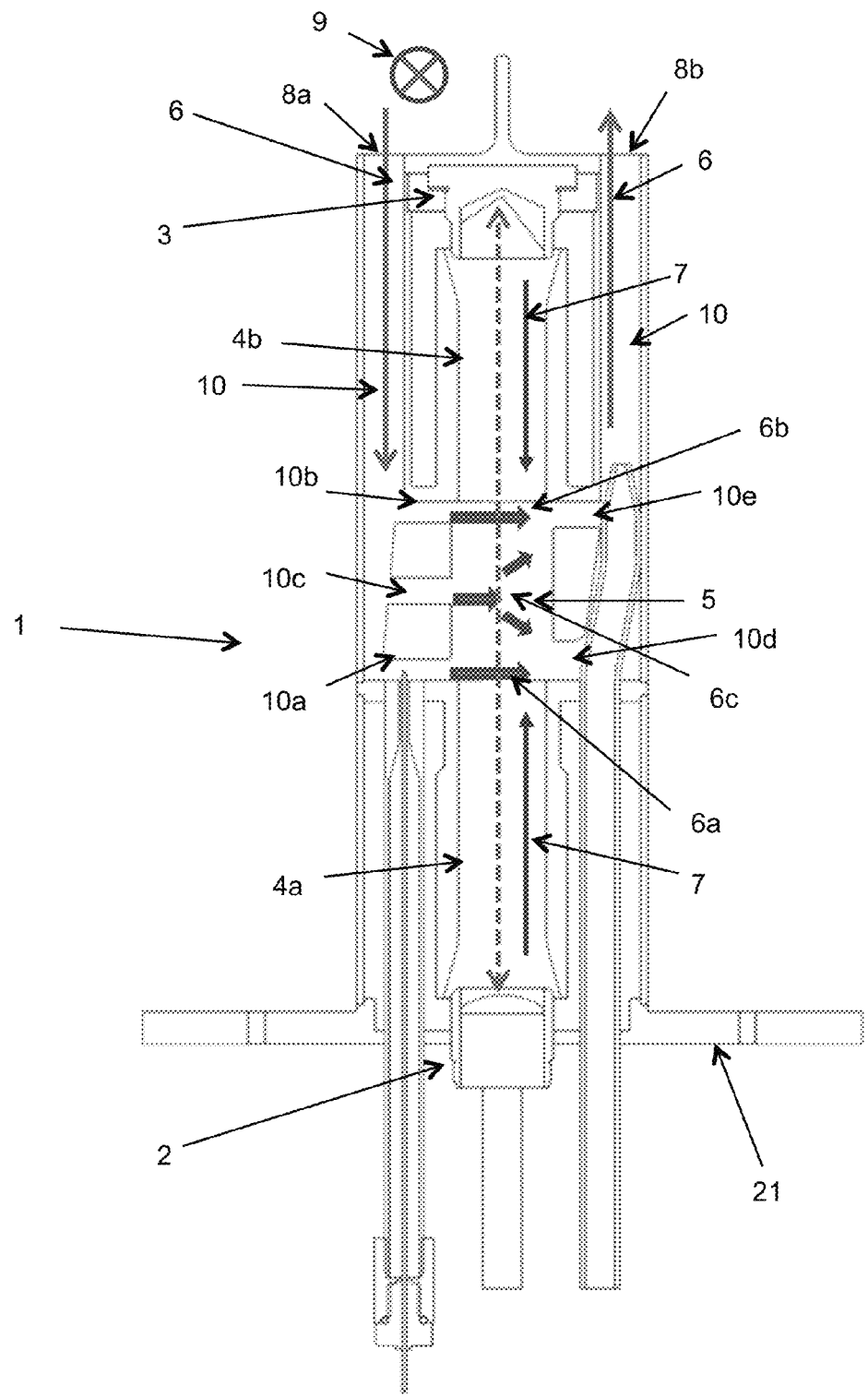
FIG. 2 Illustration of an embodiment of an aspect of a probe for a gas sensor showing the light path passing a first and second purge gas volume.

FIG. 2 shows a top view of an embodiment of the probe (1) according to the present invention.

The probe (1) comprises a light source and detector system positioned in connection to a lens (2). The detector emits light through the lens (2) towards a reflector (3) by a light path illustrated by the dashed arrow reaching from the lens (2) to the reflector (3), where it is reflected back towards and back through the lens (2) to a detector. The detector and light source is not illustrated. The emitted light passes through a first purge gas volume (4a), a measuring region (5) and a second purge gas volume (4b).

The first (4a) and second (4b) purge gas volumes are positioned between the measuring region (5) and respectively the lens (2) and the reflector (3). Purge gas (7) flows in each of the purge gas volumes (4a, 4b) in the direction towards the measuring region (5) thus preventing gas or other substances and particles in the measuring region (5) from entering into the purge gas volumes (4a, 4b) by the flow of purge gas, this thus forming a protection or curtain for respectively the lens (2) and reflector (3). The purge gas (7) thus flows essentially in directions parallel to the light path, at least in the areas of the purge gas volumes (4a, 4b).

In some embodiment of the present invention the probe (1) comprises none or only one of the first (4a) and second (4b) purge gas volumes.

The purge gas (7) could be a specific gas or just air (e.g. being filtered or cleaned) conveyed into the system.

The probe (1) comprises a sample inlet (8a) being in flow communication with the flow of gas (9) to be measured, and where this sample inlet (8a) is in flow communication with a sample gas conduit (10) being connected to the measuring region (5) by three branches (10a, 10b, 10c). Each of the branches in one embodiment has different flow restrictions, or alternatively as in the illustrated embodiment, the sample gas conduit (10) changes flow restriction in the sections between the branches (10a, 10b, 10c). The sample gas (6) entering the sample inlet (8a) (such as being dragged into the sample inlet (8a) from the flow of gas (9) by e.g. a venturi pump) is by the branches (10a, 10b, 10c) splits into three flows entering the measuring region (5). With different flow restrictions in the branches (10a, 10b, 10c) it is possible to regulate the individual three flows rates (6a, 6b, 6-c) such that they are the same or alternatively so that two or all of them are different.

In the illustrated embodiment the branches (10a, 10b, 10c) formed by two 'flow guides positioned as walls between the sample gas conduit (10) and the measuring region (5), and where the different flow restrictions are formed by a slope of the walls of these 'flow guides' directing towards the sample gas conduit (10) thus changing its cross section area and thereby the flow restriction. Alternative embodiments could be introduced such as inserting glass capillary tubes of different lengths and/or internal diameters.

The illustrated embodiment shows three branches (10a, 10b, 10c) splitting the sample gas (6) into three flows (6a, 6b, 6c), but an alternative embodiment only comprises two flows (6a, 6b) and two branches (10a, 10b). In this embodiment the first flow (6a) enters the measuring chamber (5) in the area close to the first purge gas volume (4a) and the second flow (6b) in the area close to the second purge gas volume (4b) and are in this manner adapted to remove purge gas (7) entering the measuring region (5) from the first (4a) and second (4b) purge gas volume respectively, especially from a middle region of the measuring region (5) such that this middle region comprises sample gas (6) un-mixed with purge gas (7). If the sample gas (6) was mixed with the purge gas (7) its concentration would be altered and thus the measurements affected. It has however been found often to be difficult filling the middle region with sample gas (6) having only the first and second flows (6a, 6b) and therefore to this purpose in the illustrated embodiment of the present invention a third branch (10c) is introduced forming a third flow (6c) feeding the middle region.

A sample outlet (8b) for expelling the sample gas (6) from the probe (1) after it has left the measuring region (5) and where said sample outlet (8b) is positioned in flow communication with the flow of gas (9) to be measured.

The measuring region (5) is connected to the sample outlet (8b) through at least two outlets branches (10d, 10e) of the section of the sample gas conduit (10) connecting the measuring region (5) to the sample outlet (8b). In the preferred there are only two outlet branches (10, 10e) to guide the flows (6a, 6b, 6c) correctly through the measuring region (5) to fill it. In other configurations it has been found by simulations that undesired turbulences may be formed preventing the sample gas (6) from filling the measuring region (5), especially its middle region.

The sample gas (6) as it enters the sample gas conduit (10) is directed into the measuring region (5) as thee flows (6a, 6b, 6c) that may have similar or different flow rates. The inlet outlet regions of the measuring region (5) are each connected to a separate outlet branch (10d, 10e) such that the first flow (6a) and second flow (6b) passes, or transverses, the measuring region (5) with an angle relative to the direction of the light path and/or the flow of the purge gas (7) being higher than 45 degrees, or more specifically higher than 60 degrees or more specifically in the area around 90 degrees thus being essentially perpendicular thereto. The first (6a) and third (6c) flows in their flow from the respective branches (10*a*, 10*c*) to the respective outlet branches (10*d*, 10*e*) will drag the entering purge gas (7) along and out of the measuring region (5) thereby preventing it from getting in contact with the middle region and the second flow (6*b*) inferring with the measurements.

In the same manner the second flow (6*b*) transverses the measuring region (5) at an angle relative to the direction of the light path and/or the flow of the purge gas (7) being higher than 45 degrees, or more specifically higher than 60 degrees or more specifically in the area around 90 degrees thus being essentially perpendicular thereto, but where this may change as it passes as it may leave the measuring region (5) through one or both of the outlet branches (10*b*, 10*e*) also being used by the first (6*a*) and third (6*c*) flows. Preferably it enters the measuring region (5) by an angle in the range around 90 degrees.

The probe (1) in the illustrated embodiment is positioned in connection with the flow of gas (9) in a manner where sample inlet (8*a*) is at an angle relative to the flow direction of the gas (9) to be measured being higher than 45 degrees, or more specifically higher than 60 degrees or more specifically in the area around 90 degrees thus being essentially perpendicular thereto. The same applies to the sample outlet (8*b*). Further, the sample gas (6) enters the probe (1) from a sample inlet (8*a*) positioned behind the reflector (3) seen in the direction of the emitted light from the lens (2).

Introducing a sample inlet (8*a*) in a manner where it is positioned with an angle to the flow of gas such as close to 90 degrees it is ensured the gas does not itself tend to flow into the probe (1) but is dragged into the sample inlet (8*a*) e.g. by a venturi pump whereby it is it is possible to control the flowrates within the probe (1). This is unlike e.g. EP 2 604 999 where the inlets are positioned in the flow path of the gas such that it enters directly into the probe. An disadvantage with the this construction is e.g. the free passage of gasses to the measuring region making it hard to empty the measuring region from gasses during calibration as it would require a significant pressure to overcome the forces of pressure from the freely flowing gasses. The flow rates in the measuring region thus depend on flows and other conditions not controllable by the sensor system.

By dragging the gas into the sample inlet (8*a*) the exchange rate of sample gas (6) within the measuring region (5) will be well known and defined just as it eases the task of emptying the measuring region (5) for calibration as to be described below, the flow rates and response times will be well defined and controllable.

To avoid mixing the sample gas (6) expelled from the sample outlet (8*b*) with the sample gas (6) entering the sample inlet (8*a*), an extension (11) is positioned between the sample inlet (8*a*) and sample outlet (8*b*) reaching out from the probe (1) into the flow of the gas (9).

Figure 3:
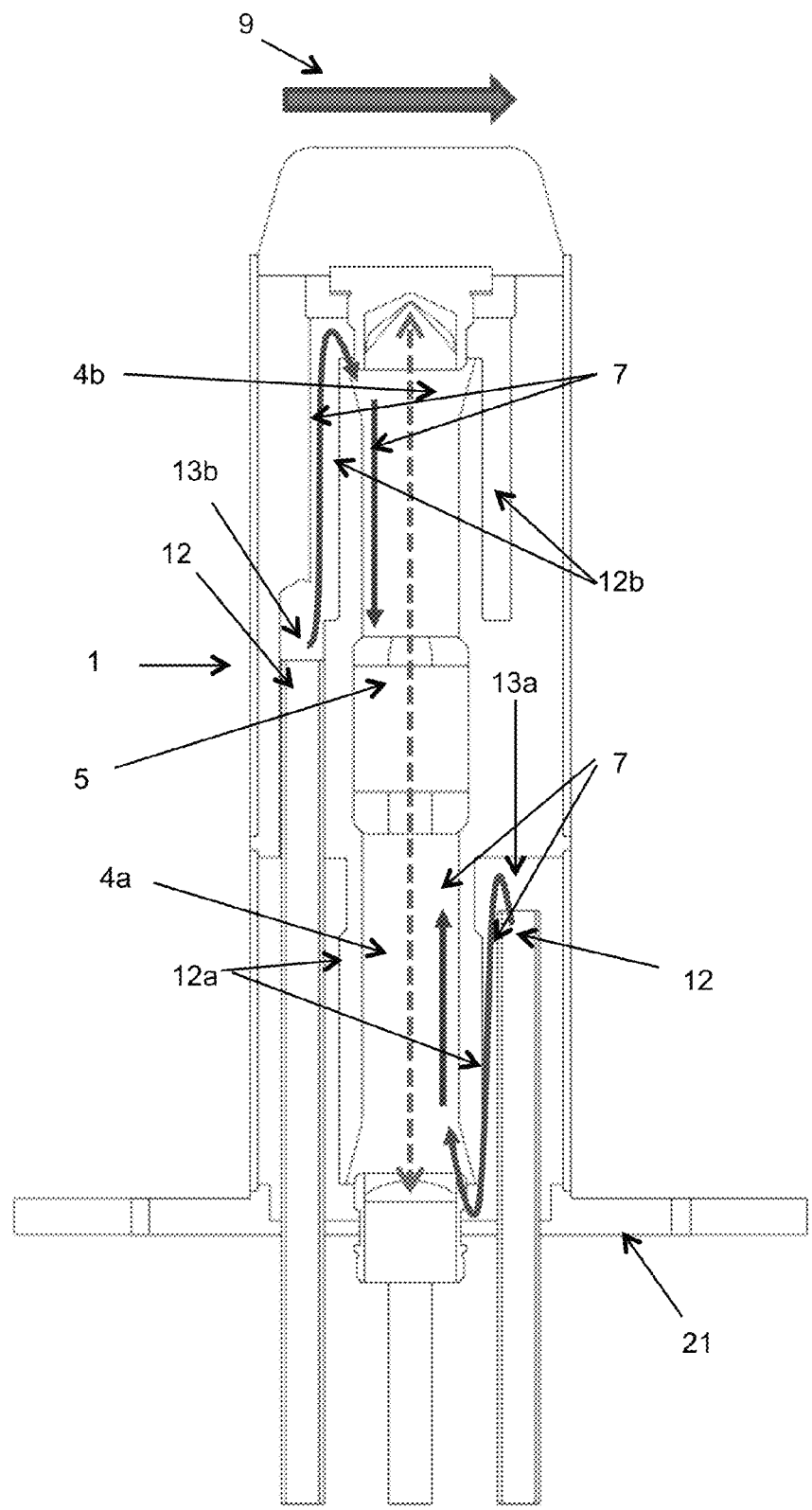
FIG. 3 Illustration of an embodiment of a second aspect of a probe for a gas sensor showing a purge gas supply path first and second purge gas volumes.

FIG. 3 shows a further feature of the present probe (1) showing it in a top-view and having a supply path (12) of purge gas (7) to the first purge gas volume (4*a*) comprises a first encircling section (12*a*) surrounding the first purge gas volume (4*a*) having a point inlet (13*a*) situated in the end close to the measuring region (5), thus distal to the lens (2), wherefrom the purge gas spreads to the full circumference of said first encircling section (12*a*) and enters said first purge gas volume (4*a*) in the end close to the lens (2). The encircling section (12*b*) may be formed as one coaxial chamber to the first purge gas volume (4*a*) or as a number of individual conduits extending from the supply path (12) to inlets to the first purge gas volume (4*a*) situated in the end proximal to the lens (2). In the present context 'point inlet' is to be understood in the sense that the flow path (12) changes from being narrow, cross section area is significantly smaller than the cross section area of e.g. the first purge gas volume (4*a*), but it spreads into an substantially wider first encircling section (12*a*) having cross section area larger than that of e.g. the first purge gas volume (4*b*).

Figure 4:
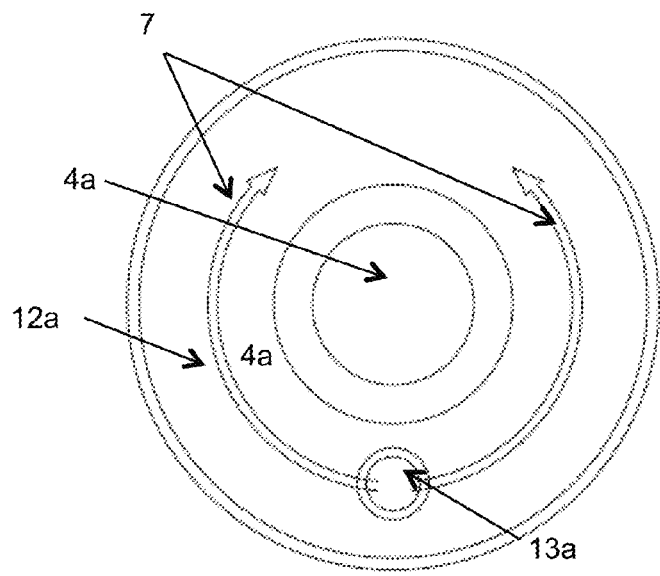
FIG. 4 Illustration of a purge gas supply path encircling a purge gas volume from a point like inlet.

FIG. 4 shows a cross section view of the encircling section (12*a*) at the point inlet (13*a*) with the purge gas (7) spreading from the supply path (12) through the point inlet (13*a*) having a cross section area smaller than that of the encircling section (12*a*) and purge gas volume (4*a*).

Figure 5:
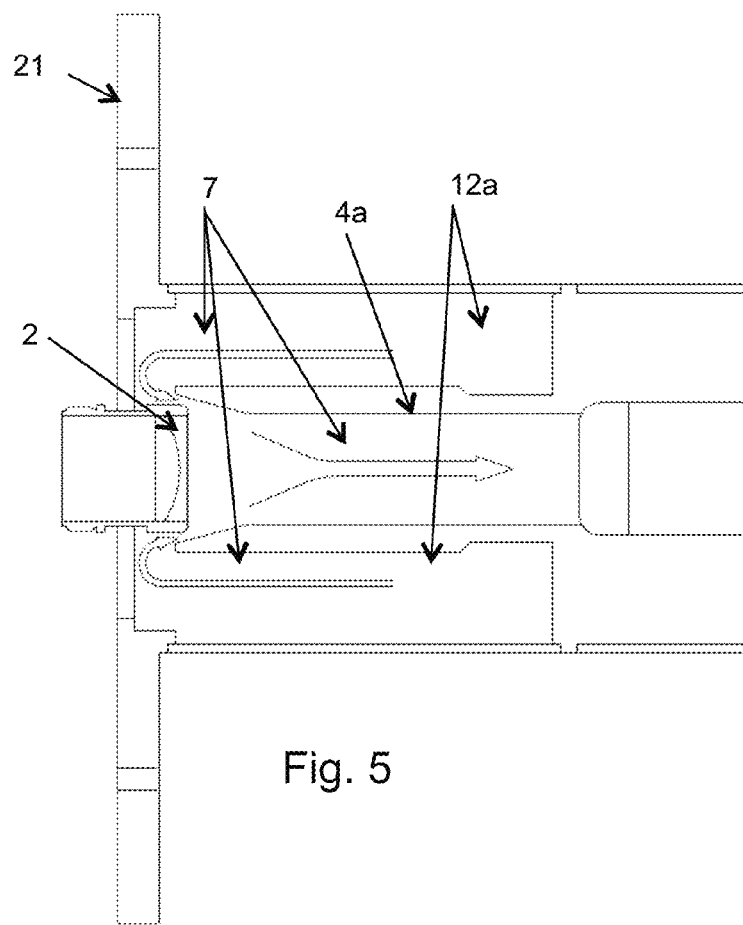
FIG. 5. Illustration of the encircling purge gas supply path showing the purge gas entering at a position close to the measuring region and entering the purge gas volume at a position distal to the measuring region.

FIG. 5 shows a top view of the section around the lens (2) showing the purge gas (7) entering from the encircling section (12*a*) to the purge gas volume (4*a*) in a substantially uniform manner around the circumference of the lens (2) forming a laminar flow in the purge gas volume (4*a*).

In the same manner and formed similar or differently to the first encircling section (12*a*), the present probe (1) may comprise a supply path (12) of purge gas (7) to the second purge gas volume (4*b*) that comprises a second encircling section (12*b*) surrounding the second purge gas volume (4*b*) and having a point inlet (13*b*) situated in the end close to the measuring region (5), thus distal to the reflector (3), wherefrom the purge gas spreads to the full circumference of said second encircling section (12*b*) and enters said second purge gas volume (4*b*) in the end close to the reflector (3).

The setup having the point inlets (13*a*, 13*b*) positioned at a distance relative to the lens (2) and reflector (3) respectively and then spreading in a circumference manner around the first and second purge gas volumes (4*a*, 4*b*) helps distributing the entering purge gas (7) uniformly in the circumference of the lens (2) and reflector (3), otherwise there would be differences in the incoming purge gas (7) inside the purge gas volumes (4*a*, 4*b*) thus forming turbulences that might actually help particles in entering from measuring region (5) into the purge gas volumes (4*a*, 4*b*), rather than preventing it.

The present probe (1) further is capable to operate in an operation mode and a calibration mode. The sample gas (6) only flows in the operation mode whereas the purge gas (7) flows both in the operation and calibration modes, where it operates as purge gas (7) during the operation mode according to the previous description, but is being used as calibration gas in the calibration mode, where the sample gas (6) flow is closed.

To prevent gas (9) from entering the system during calibration mode it has been found sufficient maintaining or increasing the flow of purge gas (7) in the system. In this manner purge gas (7) are conveyed out of the sample inlet (8*a*) and sample outlet (8*b*) in the direction against the gas (9) thus expelling the gas (9) before into the system by sample inlet (8*a*) and sample outlet (8*b*). Purge gas (7) is also conveyed out of the sample outlet (8*b*) during normal operation as also described above, but prevented from entering the part of the sample gas conduit (10) connected to the sample inlet (8*a*) by a valve or other means, or simply by the flow of sample gas (6) in the system.

The calibration mode includes closing for the sample gas (6) entering the measuring region (5) letting the purge gas flow for a given time period of time to empty the measuring region (5) of sample gas (6) and then making calibration measurements. The purge gas (7) is therefore of a known composition having a well-defined and known absorption spectrum, and may in one embodiment dried before entering the supply paths (12) to ensure it is clean of particles and moist that might influence the calibration measurements.

As also described above, due to the position of the sample inlet (8*a*) and that the sample gas (6) is dragged into the probe (1) and directed to the measuring region (5) rather than flowing directly into it, all flows within the probe (1) is controllable and it does not require to counter act the forces of the gas to keep it out as in the cases of the probes where there is direct gas access to the measuring region.

While the present disclosure has been illustrated and described with respect to a particular embodiment thereof, it should be appreciated by those of ordinary skill in the art that various modifications to this disclosure may be made without departing from the spirit and scope of the present disclosure.

What is claimed is:

1. A probe for sensor, said sensor being adapted to measure the concentration of at least one substance of a sample gas based on spectrum absorption, said probe comprising a light path passing a measuring region, wherein the sample gas are split and enters the measuring region in at least two flows, wherein the probe comprises a sample inlet being in flow communication with the flow of gas to be measured, and wherein the sample inlet is in flow communication with a sample gas conduit which splits into a first branch and a second branch being the inlets to the measuring region for a first flow and a second flow of the at least two flows, respectively.

2. The probe according to claim 1, wherein the first flow are feed into the measuring region in an area close to a first purge gas volume.

3. The probe according to claim 1, wherein the second flow are feed into the measuring region in an area close to a second purge gas volume.

4. The probe according to claim 1, wherein the sample gas transverse the measuring region with an angle to the light path being higher than 45 degrees.

5. The probe according to claim 4, wherein the first branch and the second branch have a relative different flow restriction.

6. The probe according to claim 4, wherein a third flow of the sample gas are feed into the measuring region between the first flow and the second flow through a third branch of the sample gas conduit.

7. The probe according to claim 6, where the first flow leaves the measuring region through a first outlet and the second and third flows leave the measuring region through a common second outlet.

8. The probe according to claim 6, wherein at least two of the branches have relative different flow restrictions.

9. The probe according to claim 1, wherein the sample gas enters the probe from the sample inlet and where the sample gas enters the probe in a transverse direction with an angle compared to the flow direction of the gas to be measured being higher than or equal to about 45 degrees.

10. The probe according to claim 9, wherein the probe has a sample outlet for expelling the sample gas from the probe after it has left the measuring region and where said sample outlet is positioned in flow communication with the flow of gas to be measured and where an extension positioned between the sample inlet and sample outlet that reaches out from the probe into the flow of the gas preventing the sample gas expelled from the sample outlet from mixing with the gas entering the sample inlet.

11. The probe according to claim 1, wherein the probe further encloses a lens situated in the light path between a light source and the measuring region and a purge gas flows in a first purge gas volume in the direction from the lens towards the measuring region.

12. The probe according to claim 5, wherein the probe further encloses a reflector situated at the opposite end of the measuring region relative to a lens and where a purge gas flows in a second purge gas volume in the direction towards from the reflector towards the measuring region.

13. The probe according to claim 1, wherein the sample gas are dragged into the probe through said sample inlet the flow of sample gas thus depending on the dragging forces.

14. The probe according to claim 13, wherein the sample gas is dragged into the probe by a venturi pump.

15. The probe according to claim 2, wherein the second flow are feed into the measuring region in the area close to a second purge gas volume.

16. The probe according to claim 2, wherein the sample gas transverse the measuring region with an angle to the light path being higher than 45 degrees.

17. A probe for a sensor, the sensor being adapted to measure the concentration of at least one substance of a sample gas based on spectrum absorption, the probe comprising:
   a housing defining a sample inlet and a measuring region; and
   a sample gas conduit disposed within the housing and fluidly connected to the sample inlet, the sample gas conduit including at least a first branch and a second branch creating a first flow path and a second flow path, respectively, which fluidly connect the sample inlet to the measuring region, such that the sample gas flows from the sample inlet to the measuring region by splitting into a first gas flow through the first branch and a second gas flow through the second branch.

18. The probe according to claim 17, wherein the sample gas conduit further includes a third branch creating a third flow path, which fluidly connects the sample inlet to the measuring region such that the sample gas flows from the sample inlet to the measuring region by splitting into a third gas flow through the third branch.

19. The probe according to claim 18, wherein the first branch, second branch and third branch are parallel to one another.

20. The probe according to claim 19, further comprising a light path extending in a direction perpendicular to the direction of the first, second and third branches.

* * * * *